US010874618B2

(12) United States Patent
Grmas et al.

(10) Patent No.: US 10,874,618 B2
(45) Date of Patent: Dec. 29, 2020

(54) COMPOSITIONS FOR TREATMENT OF HEART FAILURE IN DOGS

(71) Applicant: Elanco Tiergesundheit AG, Indianapolis, IN (US)

(72) Inventors: Jernej Grmas, Ljubljana (SI); Zdenka Jerala-Strukelj, Ljubljana (SI); Sebastjan Reven, Ljubljana (SI)

(73) Assignee: Elanco Tiergesundheit AG, Greenfield, IN (US)

( * ) Notice: Subject to any disclaimer, the term of this patent is extended or adjusted under 35 U.S.C. 154(b) by 176 days.

(21) Appl. No.: 14/366,900

(22) PCT Filed: Dec. 19, 2012

(86) PCT No.: PCT/EP2012/076100
§ 371 (c)(1),
(2) Date: Jun. 19, 2014

(87) PCT Pub. No.: WO2013/092673
PCT Pub. Date: Jun. 27, 2013

(65) Prior Publication Data
US 2014/0363505 A1 Dec. 11, 2014

(30) Foreign Application Priority Data

Dec. 21, 2011 (EP) .................................. 11195015
Sep. 24, 2012 (EP) .................................. 12185714

(51) Int. Cl.
*A61K 9/24* (2006.01)
*A61K 9/50* (2006.01)
*A61K 9/16* (2006.01)
*A61K 31/55* (2006.01)
*A61K 31/501* (2006.01)

(52) U.S. Cl.
CPC ............ *A61K 9/209* (2013.01); *A61K 9/1676* (2013.01); *A61K 9/5073* (2013.01); *A61K 31/501* (2013.01); *A61K 31/55* (2013.01); *A61K 9/1652* (2013.01); *A61K 9/5026* (2013.01); *A61K 9/5078* (2013.01)

(58) Field of Classification Search
None
See application file for complete search history.

(56) References Cited

U.S. PATENT DOCUMENTS

| | | | |
|---|---|---|---|
| 5,364,646 A | 11/1994 | Gruber | |
| 6,162,802 A | 12/2000 | Papa et al. | |
| 2005/0203097 A1 | 9/2005 | Folger et al. | |
| 2008/0268049 A1* | 10/2008 | Dhaliwal | A61K 9/209 424/474 |
| 2010/0035889 A1 | 2/2010 | Daemmgen et al. | |
| 2010/0183718 A1 | 7/2010 | Ovaert et al. | |

FOREIGN PATENT DOCUMENTS

| | | |
|---|---|---|
| EP | 1490037 B1 | 3/2008 |
| GB | 2394660 A | 5/2004 |
| JP | 2005-281283 | 10/2005 |
| WO | 2011/111066 | 9/2001 |
| WO | 2002/049645 A1 | 6/2002 |
| WO | 03/075842 A2 | 9/2003 |
| WO | 03/075895 | 9/2003 |
| WO | 05/037278 A2 | 4/2005 |
| WO | 2006/085208 A2 | 8/2006 |
| WO | 2008/021875 A2 | 2/2008 |
| WO | 2008/095263 A1 | 8/2008 |
| WO | 2010/097501 A2 | 9/2010 |

OTHER PUBLICATIONS

Bangalore et al. (The American Journal of Medicine (2007) 120, 713-719).*
Gana et al. (Journal of Pharmaceutical and Biomedical Analysis 27 (2002) 107-116).*
Remya et al. (International Journal of PharmTech Research vol. 2, No. 2, pp. 1250-1255).*
Haggstrom et al.; "Effect of Pimobendan or Benazepril Hydrochoride on Survival Times in Dogs with Congestive Heart Failure Caused by Naturally Occurring Myxomatous Mitral Valve Disease: The QUEST Study", J. Vet. Intern. Med (2008) 22(5): 1124-1135.
Atkins et al., "Guidelines for the Diagnosis and Treatment of Canine Chronic Valvular Heart Disease," J. Vet. Intern. Med. 2009; 23: 1142-1150.
De Madron et al., "Survival and echocardiographic data in dogs with congestive heart failure caused by mitral valve disease and treated by multiple drugs: A retrospective study of 21 cases," Can. Vet. J. 2011, vol. 52, 1219-1225.
Lombard, W., "Clinical efficacy of pimobendan (Vetmedin) in double-blind clinical trial," Vetcontact Small Animal Practice, Jul. 21, 2004.
O'Grady et al., "Effect of Pimobendan on Case Fatality Rate in Doberman Pinschers with Congestive Heart Failure Caused by Dilated Cardiomyopathy," J. Vet. Intern. Med. 2008; 22: 897-904.
Divya et al., "Bilayer tablet technology: An overview," Journal of Applied Pharmaceutical Science 01 (08); 2011: 43-47.
Deshpande et al., "Bi-layer Tablets—An Emerging Trend: A Review," IJPSR 2011, vol. 2(10), 2534-2544.
Lotensin (benazepril hydrochloride) Tablet, NDA 19851/s034 Approved Feb. 2, 2007, 1-18.
Vetmedin, Freedom of Information Summary, Apr. 3, 2007, NADA, 141-144.
Rompp Chemie Lexikon (1989-1992), 9th ed.; editor: Jurgen Falbe und Manfred Regnitz, Georg Thieme Verlag Stuttgart New York, 1992, p. 1641.
EP2793866B1—Notice of Opposition, dated Aug. 23, 2016.
EP2793866B1—Reply of the patent proprietor to the Notice of Opposition, dated Jan. 30, 2017.
EP2793866B1—Annex to the communication—opposition, dated Feb. 22, 2017.

(Continued)

*Primary Examiner* — Patricia Duffy
*Assistant Examiner* — Garen Gotfredson
(74) *Attorney, Agent, or Firm* — Joseph M. Pletcher

(57) ABSTRACT

The invention relates to a new fixed dose combination of benazepril with pimobendan.

2 Claims, No Drawings

(56) References Cited

OTHER PUBLICATIONS

EP2793866B1—Response to communication from the Opposition Division, dated Aug. 3, 2017.
Amlodipine—excerpt from Wikipedia, Jun. 2, 2017.
EP2793866B1—Response to Summons—Jun. 16, 2017.
EP2793866B1—Decision re Opponent 1 Submissions for Oral Proceedings—Jul. 10, 2017.
Chetboul et al., "Comparative Adverse Cardiac Effects of Pimobendan and Benazepril Monotherapy in Dogs with Mild Degenerative Mitral Valve Disease: A Prospective, Controlled, Blinded, and Randomized Study," J. Vet. Intern. Med. 2007; 21: 742-753.
EP2793866: Information about the result of oral Proceedings, dated Dec. 15, 2017.
D31 Statement of Grounds for Appeal by Boehringer Ingelheim Vetmedica GmbH, European Patent EP2793866B1, Appeal File No. T1131/18-3.3.07.
D32 Lachmann et al., "The Theory and Practice of Industrial Pharmacy", $3^{rd}$ ed. 1086, pp. 330/331. Lea & Febiger, US (editor), pp. 330/331 ("D32").
D34 Parikh, "Handbook of Pharmaceutical Granulation Technology", 1997, Marcel Dekker, Inc., New York, Basel, Hongkong, pp. 7-23 ("D34").
D35 Serno et al., "Granulieren", 2. Auflage 2017, Editio Cantor Verlag, Aulendorf, DE, pp. 10-37 ("D35").
D36 BI Request for correction of written decision and minutes filed Jul. 13, 2018 ("D36").
Jonathan N. King et al., Evaluation of a fixed-dose combination of benazepril and pimobendan in dogs with congestive head failure: a randomized non-inferiority clinical trial, J Vet Sci 2018, 19(1), 117-128.
Fortekor Plus: EPAR—Product Information, first published Oct. 8, 2015, last updated Nov. 11, 2018.
Summary of Product Information for Fortekor Plus, European Medicines Agency, published Oct. 8, 2015.

\* cited by examiner

COMPOSITIONS FOR TREATMENT OF HEART FAILURE IN DOGS

This application is a 371 application of PCT/EP2012/076100, filed Dec. 19, 2012; the contents of which are incorporated by reference herein.

The present invention relates to a new combination of benazepril with pimobendan, and the uses and processes for the manufacturing of such combination.

Benazepril, ((3S)-3-((2S)-1-Ethoxycarbonyl-3-phenyl-propylamino)-2,3,4,5-tetrahydro-2-oxo-1H-1-benzazepin-1-yl)acetic acid, is rapidly absorbed from the gastrointestinal tract and hydrolyzed to benazeprilat, a highly specific and potent inhibitor of angiotensin converting enzyme (ACE). It is indicated for the treatment of heart failure in dogs. It is commercially available as Fortekor® film coated tablets or flavoured tablets.

Pimobendan, (4,5-dihydro-6-(2-(4-methoxyphenyl)-1H-benzimidazol-5-yl)-5-methyl-3(2H))-pyridazinone, a benzimidazole-pyridazinone derivative, is a non-sympathomimetic, non-glycoside inotropic substance with potent vasodilatative properties. It is indicated for the treatment of canine congestive heart failure originating from valvular insufficiency (mitral and/or tricuspid regurgitation) or dilated cardiomyopathy. It is commercially available as chewing tablets or capsules under the brand name Vetmedin®.

It is well recognized by veterinarians and pet owners that oral administration of medications to pets can be very challenging. Providing means to simplify the administration of medicines to pet patients can ensure that treatments are reliably given, that the experience for the owner and pet is positive and consequently the quality of life of pets is optimal.

Combining two core recommended therapies in one single dosage form for the treatment of congestive heart failure in dogs would provide tremendous advantages as it would enable more convenient administration and by reducing the number of tablets increase compliance to the multiple therapeutic regimen advocated by veterinary cardiologists.

Accordingly, it is an objective of the present invention to provide a fixed dose combination combining benazepril, e.g. in its hydrochloride form, and pimobendan. Such a fixed dose combination drug would be convenient to use, improve veterinarian and pet owner compliance and treatment outcomes.

When combining two active ingredients in one single dosage form there is the possibility of interactions between the two active ingredients as well as between the active and inactive ingredients. In addition, the two actives may have different degradation characteristics which can lead to chemical stability issues of the final dosage form. Moreover, the release profiles of the two actives may be different which in turn will impact the pharmacological efficacy and safety of the drugs. The combination of two different active ingredients in one fixed dosage form is a technical challenge and several obstacles have to be overcome before a fixed dose combination of drugs is obtained that combines pharmacological efficacy and adequate drug stability and can be produced by a reliable and robust manufacturing method.

Both active ingredients used according to the present invention are difficult to formulate drugs. Pimobendan is a poorly water soluble drug and when administered, shows high intra- and inter-patient variability. Benazepril hydrochloride has a strongly bitter taste, is susceptible to hydrolysis and incompatible with ingredients that have an amino group.

After extensive testing the present inventors have surprisingly found a fixed dose combination that advantageously integrates all the above characteristics resulting in a practical and convenient treatment. The combination demonstrates optimal stability and release profile of both active ingredients and is a product of reliable and robust manufacturing procedure. Moreover, the fixed dose combination of the invention is surprisingly small in size and shows excellent palatability thus ensuring ease of administration.

In a first aspect the present invention provides a fixed dose combination comprising benazepril hydrochloride and pimobendan, e.g. in a ratio of 2:1, e.g. benazepril hydrochloride in an amount of 1 to 20 mg, for example 2.5, 5 or 10 mg, and pimobendan in an amount of 1 to 10 mg, for example 1.25, 2.5 or 5 mg, which fixed dose combination is in form of a tablet, e.g. a bilayer tablet. Preferably the tablet, e.g. bilayer tablet, comprises 1.25 mg pimobendan and 2.5 mg benazepril hydrochloride or 5 mg pimobendan and 10 mg benazepril hydrochloride.

In a further aspect the present invention provides the use of a fixed dose combination comprising benazepril hydrochloride and pimobendan, e.g. in form of a tablet, e.g. bilayer tablet, for the treatment of congestive heart failure in dogs, e.g. of congestive heart failure at ISACHC stage 2 and 3 (modified New York Heart Association Class II, III & IV, ACVIM class C and D) due to atrioventricular valve insufficiency or dilated cardiomyopathy in dogs.

In yet a further aspect the present invention provides a process for the manufacture of a fixed dose combination comprising benazepril hydrochloride and pimobendan in form of a bilayer tablet, wherein (a) a pimobendan formulation, e.g. in form of a granulate, is obtained, (b) a benazepril hydrochloride formulation, e.g. in form of a pellet, e.g. comprising further pharmaceutically excipients, is obtained and (c) the pimobendan and benazepril hydrochloride formulation are compressed together to form a bilayer tablet.

These and other features, advantages and objectives of the present invention will be further understood and appreciated by those skilled in the art by references to the following specification and claims.

As used herein, the term "drug" means any compound, substance, drug, medicament or active ingredient having a therapeutic or pharmacological effect, and which is suitable for administration to a mammal, e.g. a companion animal, e.g. a dog. Such drugs should be administered in a "therapeutically effective amount".

As used herein, the term "therapeutically effective amount" refers to an amount or concentration which is effective in reducing, eliminating, treating, preventing or controlling the symptoms of a disease or condition affecting a mammal. The term "controlling" is intended to refer to all processes wherein there may be a slowing, interrupting, arresting or stopping of the progression of the diseases and conditions affecting the mammal. However, "controlling" does not necessarily indicate a total elimination of all disease and condition symptoms, and is intended to include prophylactic treatment.

The appropriate therapeutically effective amount is known to one of ordinary skill in the art as the amount varies with the companion animal treated and the indication which is being addressed.

As used herein, the term "excipient" means a pharmaceutically acceptable ingredient that is commonly used in the pharmaceutical technology for preparing granulate and/or solid oral dosage formulations, e.g. pellets or tablets. Examples of categories of excipients include, but are not limited to, binders, disintegrants, lubricants, glidants, fillers and diluents. One of ordinary skill in the art may select one or more of the aforementioned excipients with respect to the particular desired properties of the granulate and/or solid oral dosage form, e.g. pellet or tablet. The amount of each excipient used may vary within ranges conventional in the art. The following references which are all hereby incorporated by reference disclose techniques and excipients used to formulate oral dosage forms. See The Handbook of Pharmaceutical Excipients, 6th edition, Rowe et al., Eds., American Pharmaceuticals Association (2011); and Remington: the Science and Practice of Pharmacy, 20th edition, Gennaro, Ed., Lippincott Williams & Wilkins (2000).

The active ingredient benazepril is generally supplied in its hydrochloride form.

Suitable excipients to formulate the benazepril layer of the fixed dose formulation of the invention include but are not limited to those disclosed in European patent EP 1 490 037 which is hereby incorporated by reference.

Benazepril pellets may be prepared according to a process described in European patent EP 1 490 037 which is hereby incorporated by reference.

The process for the production of benazepril pellets may be performed as follows:

(a) neutral-tasting, physiologically acceptable, solid, fine-grained particles with an average diameter of less than 0.8 mm, for example of 0.05 to 0.8 mm, or 0.09 to 0.8 mm, preferably 0.15 to 0.4 mm, are coated with benazepril, (b) benazepril coated particles obtained in a) are further coated with a protective, masking layer consisting of a physiologically acceptable polymer matrix.

Suitable physiologically acceptable carrier materials for producing the particles include but are not limited to cellulose, starch, saccharose, lactose or other different types of sugar. Preferably, particles made of microcrystalline cellulose, e.g. as commercially available under the name Celphere CP203®, e.g. from the company ASAHI Japan, are used.

In order to coat the particles, benazepril is conveniently dissolved in a suitable, physiologically acceptable solvent or solvent mixture, e.g. a volatile alcohol, or alcohol-water mixture, for example ethanol:water (1:1), and applied to the particles by a spraying process. Suitable solvents are known to those skilled in the art, readily volatile solvents are preferred. After the spraying procedure, the solvent or solvent mixture is removed, preferably under careful conditions, e.g. under vacuum. After the drying process, the pellets may be further sieved.

The particles coated with benazepril are preferably further coated with a protective, e.g. masking, layer consisting of a physiologically acceptable polymer matrix.

Polymers which are suitable for masking are known to those skilled in the art. Suitable classes of polymer include but are not limited to shellac, a polymer on a cellulose, acrylic acid or methacrylic acid, maleic acid anhydride, polyvinyl pyrrolidone or polyvinyl alcohol basis. Other polymers may also be considered, e.g. polymers on a cellulose basis, e.g. produced from cellulose acetate phthalate or cellulose acetate-N,N-di-n-butylhydroxypropylether. The starting materials for polymers on an acrylic acid or methacrylic acid basis may be methacrylate/methacrylic acid copolymer, 2-methyl-5-vinyl-pyridine/methacrylate/methacrylic acid copolymer, methyl methacrylate/methacrylic acid copolymer, methyl methacrylate/methacrylic acid copolymer, methyl methacrylate/maleic acid anhydride copolymer or methyl methacrylate/maleic acid anhydride copolymer.

Polymers on an acrylic acid or methacrylic acid basis are preferably used according to the present invention, e.g. polymerisation products of acrylic acid and acrylic acid esters with a low content of quaternary ammonium groups, e.g. as commercially available under the names Eudragit® E, L or S from the company Röhm, Darmstadt, Germany. Eudragit® E is a cationic polymer of dimethylaminoethyl methacrylate and a neutral methacrylic acid ester. Eudragit®L and S are anionic copolymers of methacrylic acid and methacrylic acid methylester. Eudragit®E 100 is a pH-dependent cationic polymer, which dissolves in the gastric juices at an acidic pH value of up to pH 5.0. Above pH 5.0, it is capable of swelling. In powder form, it is known and commercially available as Eudragit® EPO. Eudragit® EPO has the advantage that the process can be carried out in an aqueous medium and without organic solvents.

Masking is effected by dissolving the shellac or polymer in an organic solvent, optionally adding water, spraying the solution onto the particles which are already coated by benazepril. The solvent or solvent mixture is subsequently removed under careful conditions, e.g. under vacuum.

Suitable organic solvents for dissolution of the polymer are, for example, solvents which are relatively readily volatile, e.g. one or more of the following: methanol, ethanol, isopropanol, butanol, benzyl alcohol, ethylene glycol, propylene glycol, phenol, acetone, acetic acid, acetic acid anhydride, nitromethane, ethylene diamine, acetic acid cellosolve, e.g. an acetone—ethanol mixture, e.g. in a ratio of 1:1. Very good results are obtained by adding water, e.g. about 1 to 5 parts by volume of water to 10 to 50 parts by volume of organic solvent. Water—acetone mixtures, e.g. in a ratio of 1:30, are preferred.

Advantageously, aqueous suspensions or solutions may be used, for example coating may be carried out with Eudragit® EPO from an aqueous suspension. According to this process, safety aspects, environmental protection and economical advantages are optimally combined.

Advantageously, the size of the carrier particles is in the range of less than 0.8 mm, for example of 0.05 to 0.8 mm, or 0.09 to 0.8 mm, preferably 0.15 to 0.4 mm diameter.

Such double-coated particles, e.g. first coated with benazepril and then with the polymer matrix, may be further processed with suitable pharmaceutically acceptable excipients, e.g. fillers, disintegrants, glidants and/or lubricants, to obtain a blend, e.g. dry mixture, to form one layer of the final tablet, e.g. bilayer tablet, of the invention.

The amount of benazepril pellets in the benazepril layer is conveniently between 5 and 75%, e.g. 10%, 15%, 20%, 25%, 30%, or greater, by weight of the layer.

According to one aspect of the invention, the particle size of all excipients may be adjusted to the one of benazepril pellets, e.g. containing 5% benazepril, e.g. to a size of from 200 μm to 400 μm, e.g. between 200 μm and 350 μm, to avoid segregation during compression.

Suitable excipients to formulate the pimobendan layer of the fixed dose combination of the invention include but are not limited to those disclosed in published patent application WO 2010/055119 which is hereby incorporated by reference.

The pimobendan layer may be prepared according to a process described hereinbelow using suitable excipients known to those skilled in the art and exemplified below.

According to one aspect of the invention, the pimobendan layer may be obtained by a spray granulation process. For example, pimobendan may be introduced to the granulate partially from an aqueous/ethanolic solution and partially from an aqueous suspension. Appropriate amounts of binders, fillers and lubricants, e.g. hypromellose, lactose, starch and/or magnesiumstearate may be added to ensure compressibility. Appropriate amounts of an acid, e.g. organic acid, e.g. succinic acid, binders and disintegrants, e.g. Kollidon VA64 and/or croscarmellose sodium, may be added to ensure disintegration of tablets and dissolution of pimobendan from the fixed dose combinations, e.g. in form of tablets, e.g. bilayer tablets, of the invention.

Other pharmaceutically acceptable excipients can be added to the benazepril and/or pimobendan formulation which form part of the fixed dose combination of the invention.

Examples of pharmaceutically acceptable binders include, but are not limited to, starches; celluloses and derivatives thereof, for example, hypromellose, e.g. Pharmacoat 603; microcrystalline cellulose, e.g., AVICEL PH from FMC (Philadelphia, Pa.), Copovidone, e.g. Kollidon VA64; hydroxypropyl cellulose hydroxyethyl cellulose and hydroxylpropylmethyl cellulose METHOCEL from Dow Chemical Corp. (Midland, Mich.); sucrose; dextrose; starch corn; starch pregelatinized; corn syrup; polysaccharides; and gelatin. The binder may be present in an amount from about 0.1% to about 50%, e.g., 10-40% by weight of the composition.

Examples of pharmaceutically acceptable disintegrants include, but are not limited to, starches; starch corn; starch pregelatinized; clays; celluloses; alginates; gums; cross-linked polymers, e.g., cross-linked polyvinyl pyrrolidone or crospovidone; POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0.1% to about 10% by weight of the composition.

Examples of pharmaceutically acceptable fillers and pharmaceutically acceptable diluents include, but are not limited to, confectioner's sugar; compressible sugar; dextrates; dextrin; dextrose; lactose; lactose monohydrate; mannitol; microcrystalline cellulose, e.g. Avicel PH101 or PH102; powdered cellulose; sorbitol; sucrose and talc. The filler and/or diluent, e.g., may be present in an amount from about 15% to about 80% by weight of the composition, for example from about 15%, 25%, 35% or 45% to about 60% by weight of the composition.

Examples of pharmaceutically acceptable lubricants and pharmaceutically acceptable glidants include, but are not limited to, colloidal silica, e.g. Aerosil 200; magnesium trisilicate; starches; talc; tribasic calcium phosphate; magnesium stearate; sodium stearyl fumarate; aluminum sterate; calcium stearate; magnesium carbonate; magnesium oxide; polyethylene glycol; powdered cellulose and microcrystalline cellulose. The lubricant may be present in an amount from about 0.1% to about 5% by weight of the composition; the glidant may be present in an amount from about 0.1% to about 10% by weight.

In certain exemplary embodiments of the present invention, the composition may comprise additional excipients commonly found in pharmaceutical compositions, examples of such excipients include, but are not limited to antioxidants, antimicrobial agents, colorants, enzyme inhibitors, stabilizers, preservatives, flavors, sweeteners and other components.

These additional excipients may comprise from about 0.05-11% by weight of the total pharmaceutical composition, e.g. from about 0.5 to about 2% by weight of the total composition. Antioxidants, anti-microbial agents, colorants, enzyme inhibitors, stabilizers or preservatives typically provide up to about 0.05-1% by weight of the total pharmaceutical composition. Sweetening or flavoring agents typically provide up to about 2.5% or 5% by weight of the total pharmaceutical composition.

According to the invention therapeutically effective amounts of benazepril and pimobendan are used, e.g. 1 to 20 mg, for example 2.5, 5 or 10 mg benazepril per fixed dose combination, and 1 to 10 mg, for example 1.25, 2.5 or 5 mg of pimobendan, e.g. in the form of a tablet, e.g. bilayer tablet.

In one aspect of the invention, the fixed dose combination, e.g. in the form of a tablet, e.g. bilayer tablet, is administered to a dog in need of such treatment in an amount of 0.25 to 0.5 mg benazepril/kg and 0.125 to 0.25 mg pimobendan per kg, e.g. twice daily, e.g. 12 hours apart, e.g. in the morning and in the evening.

The fixed dose combinations of the invention are useful for the treatment of congestive heart failure (CHF) in dogs, for example of congestive heart failure at ISACHC stage 2 and 3 (modified New York Heart Association Class II, III & IV, ACVIM class C and D) due to atrioventricular valve insufficiency or dilated cardiomyopathy in dogs.

The fixed dose combinations of the invention show surprisingly good benazepril and pimobendan release characteristics, e.g. with efficacy and safety comparable to the active ingredients benazepril and pimobendan given alone as single products, e.g. as commercially available under the names Fortekor® and Vetmedin®.

A further object of the invention is directed to methods for producing the bilayer tablets described hereinbefore.

The tablet layers comprising pimobendan may be prepared by dissolving and/or suspending pimobendan in a granulation liquid, e.g. ethanol or ethanol/water mixture, together with appropriate amounts of a suitable acid, e.g. organic acid, e.g. succinic acid, a surfactant, e.g. nonionic surfactant, e.g. polysorbate 80, and/or a binder, e.g. Kollidon VA64. The granulation liquid may be sprayed on a dry mixture comprising disintegrants, fillers and other excipients conveniently used by those skilled in the art, e.g. starch, lactose and/or colorant, e.g. iron oxide colorant, e.g. iron oxide brown. Granules may be sieved after drying and a dry mixture of binders, e.g. colloidal silica, flavors, e.g. natural or synthetic meat, fish, cheese or vegetarian flavors, and lubricants, e.g. magnesium stearate, may be added.

Benazepril pellets may be conveniently obtained by those skilled in the art according to the process described hereinabove and in EP 1 490 037 which is hereby incorporated by reference.

The tablet layers comprising benazepril hydrochloride may be prepared by using benazepril pellets, containing, e.g., 2.5, 5, 10, 20, 30 or 35%, preferably 5, 10 or 20%, even more preferably 5% of benazepril, which are mixed with appropriate amounts of fillers, disintegrants, lubricants, glidants and flavors, e.g. microcrystalline cellulose, crospovidone, sucrose, e.g. as commercially available under the name Di-Pac sugar, colloidal silica and/or magnesium stearate, to obtain a blend, e.g. dry mixture, containing the active ingredient benazepril in the form of a benazepril pellets.

On the rotary tableting machine, the granulation for the first layer, e.g. comprising the pimobendan granulate, may be placed in the hopper and the machine may be adjusted until the desired weight is achieved, then the second hopper may be filled with benazepril pellets dry mixture, and the machine may be adjusted until the correct tablet weight is obtained. It will be appreciated by those skilled in the art that each layer needs precise correction to achieve uniformity of dosage for both actives.

Preferably the ratio of the compression force applied during compression of the bilayer tablet is performed at a force of 8 to 50 kN, for example at a force of 8, 10 or 17 to 30 kN, for example at a force of 17 to 29 kN.

In one aspect of the invention, the tablets, e.g. bilayer, e.g. scored, tablets, are surprisingly small in size. For example, a bilayer tablet containing 1.25 mg pimobendan and 2.5 mg benazepril may have a width of 6.5 to 7 mm, e.g. 6.6 to 6.8 mm, a length of 11.5 to 12 mm, e.g. 11.6 to 11.8 mm, and a thickness of 4.0 to 4.5 mm. A bilayer tablet containing 5 mg pimobendan and 10 mg benazepril may have a width of 10 to 10.5 mm, e.g. 10.0 to 10.2 mm, a length of 19 to 19.5 mm, e.g.19.0 to 19.2 mm, and a thickness of 6.5 to 7.5 mm.

In a further aspect of the invention, the bilayer tablets obtained by the process hereinabove described are stable at VICH conditions 30° C./65° rh, e.g. over 6, 12 or 24 months, for example over 12 months. In yet a further aspect, the tablets of the invention are stable at VICH conditions 25° C./60° rh, e.g. over 24, 36 or 48 months, for example over 36 months.

In yet a further aspect of the invention the tablets are packed in suitable packaging material, e.g. to ensure safety and stability, e.g. in child resistant packing, e.g. made of aluminium, e.g. in alu-alu blisters, as conveniently used by those skilled in the art.

The fixed dose combinations of the invention are described by the following embodiments of the invention which alone or in combination contribute to solving the objective of the invention:

1. A fixed dose combination comprising benazepril hydrochloride and pimobendan in form of a tablet, e.g. a bilayer tablet.
2. A fixed dose combination according to numbered paragraph 1 which is stable over 24 months, e.g. over 36 months at 25° C.
3. A fixed dose combination of any preceding numbered paragraph comprising 1 to 10 mg of pimobendan and 1 to 20 mg of benazepril hydrochloride.
4. A fixed dose combination of any preceding numbered paragraph comprising 1.25 mg of pimobendan and 2.5 mg of benazepril hydrochloride, or 2.5 mg of pimobendan and 5 mg of benazepril hydrochloride, or 5 mg of pimobendan and 10 mg of benazepril hydrochloride.
5. A fixed dose combination of any preceding numbered paragraph wherein the benazepril layer contains the active ingredient benazepril hydrochloride in the form of benazepril pellets.
6. A fixed dose combination of any preceding numbered paragraph wherein the pimobendan layer is in form of a granulate.
7. A fixed dose combination of any preceding numbered paragraph for use in the treatment of congestive heart failure in dogs.
8. A fixed dose combination of any preceding numbered paragraph for use in the treatment of congestive heart failure in dogs wherein the fixed dose combination is administered twice daily, e.g. 12 hours apart, e.g. in the morning and in the evening.
9. A fixed dose combination of any preceding numbered paragraph for use in the treatment of congestive heart failure in dogs wherein the release characteristics of benazepril hydrochloride and pimobendan from the fixed dose combination are equivalent to the release characteristics of benazepril hydrochloride and pimobendan when given as single products.
10. Use of a fixed dose combination of any preceding numbered paragraph for the manufacture of a medicament for the treatment of congestive heart failure in dogs.
11. A process for manufacturing of a fixed dose combination wherein
    a) a pimobendan granulate is obtained,
    b) benazepril hydrochloride pellets are obtained,
    c) the benazepril pellets obtained in b) are further mixed with excipients to obtain a blend, and
    d) the granulate and the blend obtained in a) and c) are compressed together to obtain a bilayer tablet.
12. A method for treating congestive heart failure in dogs comprising administering a fixed dose combination of any one of numbered paragraph 1 to 6.
13. A method according to numbered paragraph 12 wherein the fixed dose combination is administered twice daily, e.g. 12 hours apart, e.g. in the morning and in the evening.
14. A method according to numbered paragraph 12 or 13 wherein the release characteristics of benazepril hydrochloride and pimobendan from the fixed dose combination are equivalent to the release characteristics of benazepril hydrochloride and pimobendan when given as single products.

The following non-limiting examples further illustrate the invention.

EXAMPLES

The composition of two formulations prepared using different technological procedures is shown in the Table 1. Stability testing of the described samples was performed, results of the study are presented in the Table 2.

TABLE 1

Detailed composition of examples 1 and 2

| Pimobendan + benazepril combination | Example 1<br>5 + 20 mg<br>Monolayer tablet | Example 2<br>5 + 20 mg<br>Bilayer tablet |
|---|---|---|
| Pimobendan granule | | |
| Pimobendan | 5.00 mg | 5.00 mg |
| Succinic acid | 65.00 mg | 65.00 mg |
| Polysorbate 80 V | 10.00 mg | 10.00 mg |
| Copovidone (Kollidon) | 25.00 mg | 25.00 mg |
| Iron oxide-colorant | 2.00 mg | 2.00 mg |
| Starch corn | 60.00 mg | 60.00 mg |
| Starch pregelatinised | 60.00 mg | 60.00 mg |
| Lactose monohydrate | 557.20 mg | 557.20 mg |
| Vegeterian flavor# | 40.00 mg | / |
| Copovidone (Kollidon) | 35.00 mg | / |
| Silica colloidal | 2.40 mg | 2.40 mg |
| Magnesium stearate | 8.40 mg | 8.40 mg |
| Weight of I. layer with pimobendan | | 795.00 mg |
| Benazepril layer | | |
| Benazepril pellets | 100.00 mg (20%)* | 100.00 mg (20%)* |
| Cellulose microcrystalline | | 140.00 mg |
| Copovidone (Kollidon) | | 35.00 mg |
| Dry Flavor vegeterian | | 40.00 mg |
| Silica colloidal | | 0.50 mg |
| Stearic acid | | 2.00 mg |
| Tablet weight | 970.00 mg | 1112.50 mg |

Example 1: monolayer tablet with 5 mg of pimobendan and 20 mg of benazepril
Example 2: bilayer tablet with 5 mg of pimobendan and 20 mg of benazepril
*Alternatively, a 5% benazepril pellet formulation may be used.
Alternatively, natural or synthetic meat, fish or cheese flavor may be used.

Short description of the process:

Example 1

Pimobendan granules are prepared by dissolving a first part of pimobendan, succinic acid and polysorbate 80 in ethanol. A second part of pimobendan is dispersed in water to obtain pimobendan suspension. Water dispersion of hypromellose is mixed with pimobendan suspension to obtain final water suspension of pimobendan and hypromellose.

The prepared ethanol solution and water suspension are sprayed on the dry mixture of starch, lactose, croscarmellose sodium and colorant. Granules are sieved after drying and the dry mixture of binder, vegetarian flavor, colloidal silica and magnesium stearate are added. 870 mg of pimobendan granules (containing 5 mg of pimobendan) and 100 mg of benazepril pellets (containing 20 mg of benazepril) are mixed, and compressed into monolayer tablets with the total weight of 970 mg.

Example 2

Describes the bilayer tablets of pimobendan and benazepril. The mixtures are prepared separately. The procedure for pimobendan granules is the same as in example 1. Benazepril pellets (containing 20 mg of benazepril), are mixed with microcrystalline cellulose, binder copovidone, dry flavor vegetarian, colloidal silica and stearic acid.

On the rotary tableting machine, the granulation for the first layer is placed in the hopper and the machine is adjusted until the desired weight is achieved, then the second hopper is filled with benazepril pellets dry mixture, and the same procedure is followed until the correct tablet weight is obtained. Since weight is related to the fill volume each layer need precise correction to achieve uniformity of dosage for both actives.

used, instead of 20% benazepril pellets. Results are presented in the table 3 below, as % of formed Impurity C.

TABLE 3

Chemical stability of example 1, 2 and 3
% of Impurity C

| Sample | initial | 50° C. 7 days | 40° C. 14 days | 40° C. 1 month | 25/60 1 month |
|---|---|---|---|---|---|
| Example 1 | 0.17 | 11.62 | Not tested | 11.82 | 0.33 |
| Example 2 | <0.05 | 1.75 | Not tested | 1.62 | 0.17 |
| Example 3 | <0.05 | 1.00 | 0.59 | Not tested | Not tested |

Results, obtained at chosen stress conditions speak in favour of using 5% benazepril pellets instead of 20% benazepril pellets. With this optimization levels of formed Impurity C are reduced from previously about 2% to final 1%.

We have detected the degradation products by UPLC equipped with BEH ShieldRP18, 1.7 μm, 100×2.1 mm column which was maintained in a column oven at 55° C. The mobile phase A consisted of a mixture of methanol, water, acetic acid in volume ratio of 200:800:0.2 and 0.81 g of tetrabutylammonium bromide and mobile phase B consisted of a mixture of a methanol, water and acetic acid in ratio 800:200:0.2 (V/V/V) and 0.81 g of tetrabutylammonium bromide. The flow rate was 0.5 ml/min, using following gradient:

TABLE 2

Stability results

| Source of impurity | Relative Retention | Example 1 | | | | Example 2 | | | |
|---|---|---|---|---|---|---|---|---|---|
| | | initial | 50° C. 7 days | 40° C. 1 month | 25/60 1 month | initial | 50° C. 7 days | 40° C. 1 month | 25/60 1 month |
| BNZ | Rr-0.32 (IMPC) | 0.17 | 11.62 | 11.82 | 0.33 | <0.05 | 1.75 | 1.62 | 0.17 |
| BNZ | Rr-1.18 (IMPB) | 0.38 | 0.47 | 0.48 | 0.38 | 0.39 | 0.41 | 0.41 | 0.38 |
| BNZ | Rr-1.27 (IMPG) | 0.16 | 0.18 | 0.19 | 0.16 | 0.13 | 0.18 | 0.20 | 0.15 |
| PMB | Rr-0.61 | <0.05 | <0.05 | 0.05 | <0.05 | <0.05 | <0.05 | <0.05 | 0.05 |
| PMB | Rr-1.43 (IMPB) | 0.09 | 0.09 | 0.09 | 0.09 | 0.09 | 0.09 | 0.08 | 0.09 |
| | SUM | 0.80 | 12.36 | 12.63 | 0.96 | 0.61 | 2.43 | 2.31 | 0.84 |

* BNZ = benazepril hydrochloride,
** PMB = pimobendan

Results from stress stability study of Example 1 and Example 2 are presented in the table above. Stability of the product is reflected and evaluated by the increase of benazepril hydrolytic degradation product Impurity C. Only this impurity is seen to show increasing trends, other impurities that were detected, are present as related substances, or they don't show any increasing trends.

Levels of Impurity C are significantly lower for the bilayer tablet formulation.

Further optimization with regard to chemical stability was done according to Example 3, which has similar composition as Example 2, only that 5% benazepril pellets were

| Time (minutes) | % A |
|---|---|
| 0 | 95 |
| 7 | 95 |
| 12 | 60 |
| 17 | 20 |
| 19.5 | 20 |
| 20 | 95 | and the detection wavelength was 240 and 330 nm.

Example 4

Benazepril pellets are prepared according to the following process:

4.1 Preparation of a Solution of Benazepril

| Composition | Weight |
|---|---|
| benazepril HCl (active substance) | 2.856 kg |
| Excipients | |
| ethanol 96% | 8.16 kg |
| water | 12.24 kg |
| polyvinyl pyrrolidone | 1.071 kg |

Ethanol and water are mixed in a vessel until a homogeneous solution is formed. Benazepril hydrochloride is added to the solvent mixture and stirred for 5 minutes until a clear solution is obtained. Polyvinyl pyrrolidone is subsequently added and stirred for a further 10 minutes until a clear solution is obtained.

4.2 Coating of Particles with Benazepril

| Excipients | Weight |
|---|---|
| Celphere CP 203 ®* | 31.15 kg |

Celphere® is a commercial product of the company ASAHI, Japan. It consists of round microcrystalline cellulose particles or pellets.

Celphere® pellets are placed in a fluidised bed equipment and heated to a product temperature of 35° C. The required amount of benazepril solution obtained in step 4.1 (23.9 kg) is sprayed onto the pellets. After spraying, the pellets are dried at an admission temperature of 55° C. until attaining residual moisture of <4%. The pellets are subsequently sieved through a 0.5 mm sieve. The yield of benazepril pellets is >95%.

4.3 Masking of the Particles

| Excipients | Weight |
|---|---|
| sodium lauryl sulphate | 0.75 kg |
| dibutyl sebacate | 1.61 kg |
| Eudragit EPO ®* | 10.71 kg |
| Syloid 244 FP ® | 4.28 kg |
| water | 89.75 kg |
| Aerosil 200 ® | 0.26 kg |

Eudragit® is a commercial product of the company Rohm, Germany. It consists of butyl methacrylate-(2-dimethylaminoethyl)methacrylate-methylmethacrylate copolymer (1:2:1). Syloid 244 FP® is a precipitated silicon dioxide, which is obtainable from the company Grace GmbH, in Worms, Germany. Aerosil 200® is colloidal silicon dioxide from the company Degussa in Frankfurt/Main, Germany.

Sodium lauryl sulphate and dibutyl sebacate are dissolved in 89.75 kg of water. Subsequently, the Eudragit EPO® is added to the solution and carefully stirred for at least 3 hours until a homogeneous suspension is obtained. Syloid 244 FP® is added and the mixture is stirred until a homogeneous suspension is produced. In order to remove larger particles from the suspension, the solution is sieved through a 1.0 mm sieve before coating the benazepril pellet. During the entire coating process, the spray suspension is carefully stirred, so that no particles can settle in the vessel. Then, 35 kg of benazepril pellets are filled into the fluidised bed equipment and heated to a product temperature of 28° C. The coating suspension is sprayed onto the benazepril pellets. After spraying, the pellets are dried at an admission temperature of 55° C. until attaining residual moisture of <4%. The pellets are subsequently sifted through a 0.5 mm sieve. The yield of benazepril pellets is >90%. In order to avoid adhesion of the taste-masked pellets during storage, 0.26 kg of Aerosil 200® are sifted onto the pellets through a 1.4 mm sieve. The dry mixture is mixed for 10 minutes in a drum mixer.

Examples 5, 6 and 7

| Component | Function | Example 5 1.25 + 2.5 mg | Example 6 2.5 + 5 mg | Example 7 5 + 10 mg | Percent |
|---|---|---|---|---|---|
| Pimobendan | Active substance | 1.250 | 2.500 | 5.000 | 0.38 |
| Succinic acid | Acidifying agent | 15.000 | 30.000 | 60.000 | 4.51 |
| Polysorbate 80 | Wetting agent | 2.500 | 5.000 | 10.000 | 0.75 |
| Ethanol[1] | Granulation liquid, solvent | 170.000 | 340.000 | 680.000 | — |
| Hypromellose (Pharmacoat 603) | Binder | 6.250 | 12.500 | 25.000 | 1.88 |
| Purified water - P63[1] | Granulation liquid, solvent | 66.500 | 133.000 | 266.000 | — |
| Starch corn | Binder, disintegrant | 15.000 | 30.000 | 60.000 | 4.51 |
| Lactose monohydrate NF | Filler | 140.325 | 280.650 | 561.300 | 42.20 |
| Starch pregelatinized 1551 | Binder, disintegrant | 15.000 | 30.000 | 60.000 | 4.51 |
| Croscarmellose sodium (Ac-di-sol) | Disintegrant | 1.250 | 2.500 | 5.000 | 0.38 |
| Iron oxide brown | Coloring agent | 0.500 | 1.000 | 2.000 | 0.15 |
| Copovidone (Kollidon VA 64) | Binder | 6.250 | 12.500 | 25.000 | 1.88 |
| Croscarmellose sodium (Ac-di-sol) | Disintegrant | 2.500 | 5.000 | 10.000 | 0.75 |
| Vegetarian flavor[2] | Flavor | 8.000 | 16.000 | 32.000 | 2.41 |
| Silica, colloidal anhydrous (Aerosil 200) | Glidant | 1.075 | 2.150 | 4.300 | 0.32 |
| Magnesium stearate | Lubricant | 2.600 | 5.200 | 10.400 | 0.78 |
| Total pimobendan layer | | 217.50 | 435.00 | 870.00 | 65.41 |

-continued

| | | Example | | | |
|---|---|---|---|---|---|
| Component | Function | 5<br>1.25 + 2.5 mg | 6<br>2.5 + 5 mg | 7<br>5 + 10 mg | Percent |
| Benazepril pellets 5% | Active substance in pellets | 50.000 | 100.000 | 200.000 | 15.04 |
| Microcrystalline cellulose (Avicel PH 102) | Filler | 23.590 | 47.183 | 94.360 | 7.10 |
| Microcrystalline cellulose (Avicel PH 101) | Filler | 11.470 | 22.941 | 45.880 | 3.45 |
| Sucrose for direct compression (DiPac) | Filler, flavor | 26.760 | 53.529 | 107.040 | 8.05 |
| Crospovidon (Polyplasdone XL) | Disintegrant | 1.720 | 3.441 | 6.880 | 0.52 |
| Silica, colloidal anhydrous (Aerosil 200) | Glidant | 0.310 | 0.612 | 1.240 | 0.09 |
| Magnesium stearate | Lubricant | 1.150 | 2.294 | 4.600 | 0.34 |
| Total benazepril layer | | 115.00 | 230.00 | 460.00 | 34.59 |
| Toatal tablet mass | | 332.50 | 665.00 | 1330.00 | 100.00 |

[1]will be removed during the process
[2]alternatively, natural or synthetic meat, fish or cheese flavor may be used

Examples 5, 6 and 7

Pimobendan granules are prepared by dissolving a first part of pimobendan, succinic acid and polysorbate 80 in ethanol. A second part of pimobendan is dispersed in water to obtain pimobendan suspension. Water dispersion of hypromellose is mixed with pimobendan suspension to obtain final water suspension of pimobendan and hypromellose. The prepared ethanol solution and water suspension are sprayed on the dry mixture of starch, lactose, croscarmellose sodium and colorant. Granules are sieved after drying and mixed with Copovidone, croscarmellose sodium, flavor, colloidal silica and magnesium stearate to obtain the pimobendan layer.

Benazepril pellets (containing 5% of benazepril), are mixed with microcrystalline cellulose, sucrose for direct compression, Crospovidon, colloidal silica and magnesium stearate to obtain a benazepril blend.

On the rotary tableting machine, the pimobendan layer is placed in the hopper and the machine is adjusted until the desired weight is achieved, then the second hopper is filled with the benazepril blend, and the same procedure is followed until the correct tablet weight is obtained. Both layers are compressed to form bilayer tablets.

The invention claimed is:

1. A bilayer tablet comprising a benazepril layer and a pimobendan layer,
   wherein said benazepril layer comprises 50 mg of benazepril pellets, 35.06 mg microcrystalline cellulose, 26.76 mg sucrose, 1.72 mg crospovidone, 0.31 mg silica, colloidal anhydrous, and 1.15 mg magnesium stearate;
   wherein said benazepril pellets comprise 5 wt % benazepril hydrochloride, microcrystalline cellulose, povidone, butyl methacrylate-(2-dimethylaminoethyl) methacrylate-methylmethacrylate copolymer, silicon dioxide, anhydrous, sodium lauryl sulfate, dibutyl sebacate, and silica, colloidal anhydrous; and
   wherein said pimobendan layer comprises 1.25 mg pimobendan, 15 mg succinic acid, 2.5 mg polysorbate 80, 6.25 mg hypromellose, 15 mg maize starch, 140.325 mg lactose monohydrate, 15 mg starch pregelantinized, 3.75 mg croscarmellose sodium, 0.5 mg iron oxide brown, 6.25 mg copovidone, 8 mg flavorant, 1.075 mg silica, colloidal anhydrous, and 2.6 mg magnesium stearate.

2. A bilayer tablet comprising a benazepril layer and a pimobendan layer,
   wherein said benazepril layer comprises 200 mg of benazepril pellets, 140.24 mg microcrystalline cellulose, 107.04 mg sucrose, 6.88 mg crospovidone, 1.24 mg silica, colloidal anhydrous, and 4.6 mg magnesium stearate;
   wherein said benazepril pellets comprise 5 wt % benazepril hydrochloride, microcrystalline cellulose, povidone, butyl methacrylate-(2-dimethylaminoethyl) methacrylate-methylmethacrylate copolymer, silicon dioxide, anhydrous, sodium lauryl sulfate, dibutyl sebacate, and silica, colloidal anhydrous; and
   wherein said pimobendan layer comprises 5 mg pimobendan, 60 mg succinic acid, 10 mg polysorbate 80, 25 mg hypromellose, 60 mg maize starch, 561.3 mg lactose monohydrate, 60 mg starch pregelantinized, 15 mg croscarmellose sodium, 2 mg iron oxide brown, 25 mg copovidone, 32 mg flavorant, 4.3 mg silica, colloidal anhydrous, and 10.4 mg magnesium stearate.

* * * * *